US006303826B1

(12) United States Patent
Bhinde et al.

(10) Patent No.: US 6,303,826 B1
(45) Date of Patent: Oct. 16, 2001

(54) METHOD FOR PURIFICATION OF ACETONE

(75) Inventors: Manoj V. Bhinde, Boothwyn, PA (US); Scott R. Keenan, Marlton, NJ (US)

(73) Assignee: Sunoco, Inc. (R&M), Philadelphia, PA (US)

( * ) Notice: Subject to any disclaimer, the term of this patent is extended or adjusted under 35 U.S.C. 154(b) by 0 days.

(21) Appl. No.: 09/487,656

(22) Filed: Jan. 19, 2000

(51) Int. Cl.[7] .......................... C07C 45/90; C07C 49/08
(52) U.S. Cl. ............................ 568/411; 568/410
(58) Field of Search .................... 568/411, 410

(56) References Cited

U.S. PATENT DOCUMENTS

| | | |
|---|---|---|
| 2,083,856 | 6/1937 | Moravec et al. . |
| 2,355,140 | 10/1944 | Bludworth . |
| 2,624,699 | 1/1953 | Joris . |
| 2,701,264 | 2/1955 | Deahl et al. . |
| 2,906,675 | 9/1959 | Hall et al. . |
| 2,906,676 | 9/1959 | Bewley et al. . |
| 3,668,256 | 6/1972 | Brundege . |
| 4,329,510 | 5/1982 | Uno et al. . |
| 5,567,853 | 10/1996 | Gupta . |
| 5,788,818 | 8/1998 | Lorenzoni et al. . |

FOREIGN PATENT DOCUMENTS

| | | | |
|---|---|---|---|
| 4225291 | * | 2/1994 | (DE) . |
| 2116177 | | 9/1983 | (GB) . |
| 06157396 | * | 3/1994 | (JP) . |
| WO 01/307035 A1 | | 5/2001 | (WO) . |

OTHER PUBLICATIONS

Frennet, A. and Bastin, Control of Unregulated Emissions From Ethanol–Fueled Diesel Engines—A Study of the Effect of Catalyst Support on the Low Temperature Oxidation of Ethanol and Acetaldehyde Using Precious Metals, "Catalysis and Automotive Pollution Contol III", Proceedings of the Third International Symposium, Brussels, Belgium, Apr. 20–22, 1994, Elesevier, p. 855–869.

Pettersson, L. and Jaras, "Exhaust Gas Catalyst for Alcohol Vehicles", Kommunikations Forsknings Beredningen, Stockholm, Sweden, 1994, pp. 1–62.

Starchevskiy, M.K. et al., "Formation of Acetic Anhydride in the Nonradical Oxidation of Acetaldehyde by Oxygen in the Presence of Pd–561 Giant Clusters, " Dok. Akads. Nauk, vol. 342, No. 6, 1995, pp. 772–775.

* cited by examiner

Primary Examiner—Sreeni Padmanabhan
(74) Attorney, Agent, or Firm—Robert A. Koons, Jr.; Matthew P. McWilliams; Pepper Hamilton LLP

(57) ABSTRACT

A method for purification of acetone containing at least one oxidizable impurity. The method comprises the steps of: (a) contacting acetone containing at least one oxidizable impurity with a heterogeneous oxidation catalyst in the presence of oxygen for a time and at a temperature sufficient to oxidize at least a portion of at least one of the oxidizable impurities; and (b) substantially separating purified acetone from the resulting mixture obtained from step (a).

11 Claims, No Drawings

METHOD FOR PURIFICATION OF ACETONE

BACKGROUND OF THE INVENTION

1. Field of the Invention

The present invention relates to a method for purification of acetone containing at least one oxidizable impurity by contacting the acetone with a heterogeneous oxidation catalyst in the presence of oxygen.

2. Related Background Art

The commercial process for purifying acetone employs a distillation column which separates water and other higher-boiling impurities from the acetone. Traditionally, removal of light aldehyde impurities is accomplished by reactive distillation in which an aqueous solution of sodium hydroxide is injected into the distillation column to promote condensation of aldehydes to form higher-boiling compounds. See, e.g., U.S. Pat. Nos. 5,788,818; 5,567,853; 4,329,510; 3,668,256; 2,906,676; 2,906,675; and 2,624,699. Use of this process requires introduction of water to the distillation column to aid in removing salts and other by-products of the sodium hydroxide reaction. The presence of water, salts, and high-boiling by-products reduces the efficiency of the distillation column.

In particular, crude acetone resulting from the production of phenol from cumene typically contains about 200–700 ppm aldehydes and 200–500 ppm methanol. Treatment of acetone with aqueous sodium hydroxide during distillation leads to production of distillation bottoms containing large amounts of polymers and salts, thereby decreasing the efficiency of conventional reboilers. Moreover, base-catalyzed self-condensation of acetone reduces the yield of purified acetone. Impurity levels in commercial acetone purified by this method are still about 30–50 ppm for acetaldehyde and about 200–300 ppm for methanol. A method for purification of acetone that overcomes the aforementioned difficulties is disclosed herein.

Oxidation of aldehydes and alcohols in the presence of oxidation catalysts is well known in the art. However, applicants are not aware of any attempt to use such a method to purify acetone containing aldehyde and alcohol impurities. The mechanism of oxidation of acetaldehyde, present at high concentrations in various solvents, including acetone, by soluble palladium clusters has been studied by Starchevskiy et al., as reported in *Dokl. Akad. Nauk*, volume 342, page 772 (1995). However, this study clearly was not directed to a purification method for acetone. Indeed, this reference provides no indication as to whether the soluble palladium catalyst reduced acetaldehyde to ppm levels in acetone, or the extent of acetone decomposition encountered during the oxidation. For these reasons, Starchevskiy et al. do not provide a method that would allow efficient purification of acetone by selective oxidation of impurities.

Applicants are not aware of any use of oxidation catalysts in purification of acetone, despite the commercial quantities of acetone produced worldwide by a variety of processes. An efficient process for purification of acetone would be highly desirable.

SUMMARY OF THE INVENTION

The present invention is directed to a method for purification of acetone containing at least one oxidizable impurity. The method comprises the steps of: (a) contacting acetone containing at least one oxidizable impurity with a heterogeneous oxidation catalyst in the presence of oxygen for a time and at a temperature sufficient to oxidize at least a portion of at least one of the oxidizable impurities; and (b) substantially separating purified acetone from the resulting mixture obtained from step (a).

DETAILED DESCRIPTION OF THE INVENTION

In the method of the present invention, impure acetone is contacted with a heterogeneous oxidation catalyst in the presence of oxygen. The impure acetone contains at least one oxidizable impurity, i.e., an impurity readily susceptible to oxidation. Such impurities include without limitation aldehydes, alcohols, benzylic compounds and alkenes. The method of the present invention successfully reduces or removes oxidizable impurities from acetone without oxidizing a substantial portion of the acetone. Suitable oxidation catalysts are those capable of oxidizing alcohols, aldehydes, benzylic compounds and alkenes. Typically, commercial crude acetone is obtained from the cumene oxidation process, and contains acetaldehyde, methanol, and smaller amounts of propionaldehyde and cumene, among other impurities. Typically, commercial crude acetone contains no more than about 700 ppm of aldehyde impurities and no more than about 300 ppm of methanol. Preferably, the method of this invention is practiced on an acetone stream containing less than about 1000 ppm of aldehyde impurities and less than about 500 ppm methanol. Preferred oxidation catalysts are those capable of oxidizing alcohols and aldehydes.

Suitable oxidation catalysts for use in the method of this invention include without limitation precious metals or other transition metals supported on carbon or inorganic materials (i.e., supported catalysts) and precious metals or other transition metals in substantially pure form. Preferred catalysts are precious metals supported on carbon, or on inorganic supports. Inorganic supports include without limitation alumina, silica, clay, titania/zirconia, and magnesia. Alumina and silica supports are preferred. Palladium is the most preferred of the precious metals. The most preferred catalyst is palladium on α-alumina.

The Examples presented hereinafter demonstrate that there is considerable variation in the efficiencies of various metals and supports. Either palladium on carbon or palladium on silica provides a high percentage conversion of aldehydes and alcohols to their oxidized forms, as shown in Examples 1, 2, 4 and 7. However, the consumption of acetone ("acetone burn") is higher for the silica support. Palladium on alumina gives variable results depending on the type of alumina used. When the support is a relatively low-surface-area α-alumina, as in Example 8, high percentage conversions of aldehydes and methanol are obtained with very low consumption of acetone and with relatively low levels of byproducts. However, when the support is a relatively high-surface-area γ-alumina, although percent conversions for both acetaldehyde and methanol are roughly comparable to those obtained with an α-alumina or silica support, initially increased consumption of acetone and formation of byproducts are observed, as shown in Example 9. The Pd/γ-alumina catalyst produces high initial levels of byproducts, with little of the expected acetic acid oxidation product, but appears to stabilize at longer times, producing lower levels of byproducts. Platinum on carbon, ruthenium on carbon, and manganese nodules provide lower conversions, especially for acetaldehyde, as shown in Examples 3, 5 and 6, respectively. Manganese nodules also appear actually to promote the formation of methanol at higher temperatures.

Oxygen is introduced into the reaction vessel as air, as pure oxygen, as a mixture of oxygen or air with one or more non-oxidizable gases, including without limitation nitrogen, and the noble gases, or from a compound which serves as an oxygen source, including without limitation nitrous oxide, hydrogen peroxide, and organic peroxides and hydroperoxides.

After at least a portion of at least one of the oxidizable impurities is oxidized, purified acetone is separated from the mixture, either as a vapor, or as a liquid. The heterogeneous catalyst typically is removed from the vapor or liquid components by filtration. This may be achieved by using the catalyst in the form of a fixed or fluidized bed from which the liquid components are separated by filtration as part of the normal operation of the catalyst bed, or by a separate filtration operation designed to remove an insoluble catalyst from a vapor or liquid product. Purified acetone typically is separated from the oxidized impurities by distillation of the lower boiling acetone. Typically, purified acetone containing less than about 10 ppm acetaldehyde and less than about 100 ppm methanol is obtained from a commercial acetone stream using the method of this invention.

Suitable operating temperatures, pressures and times are interdependent, and will also vary depending on the amount and type of catalyst used, flow rates of acetone and oxygen, and the desired acetone purity level. Preferably, the reaction temperature is at least about 50° C. to achieve rapid oxidation of the impurities, and below about 250° C. to minimize combustion of acetone. The preferred pressure range for the reaction is 0–100 psig (101–791 kPa). Most preferably, the reaction is carried out in the vapor phase, and the reaction temperature is in the range from about 125° C. to about 200° C. In this temperature range, the preferred pressure range is 0–100 psig (101–791 kPa). Whether the acetone is substantially in the liquid or vapor phase during the oxidation will be determined by the choices of catalyst and operating conditions, and is not critical to the success of the present method.

The following Examples are intended solely to illustrate certain preferred embodiments of the invention, and not to limit the invention.

EXAMPLES

Example 1

Abatement of Acetaldehyde, Propionaldehyde and Methanol in Acetone Using a 1% Pd/C Catalyst.

Description of Reactor

The experiments were conducted in a single-stage continuous gas-phase reactor. Catalyst (1–10 mL) was loaded into a 0.5 inch (1.27 cm) O.D.×12 inch (30.5 cm) long stainless steel tubular reactor. The temperature in the reactor was controlled by a clam-shell heater surrounding the reactor. Acetone feed containing impurities was pumped into the reactor at 0.1–1 mL/min through a pre-heater/mixer tube packed with glass beads and heated to about 110–120° C., in which it mixed with an air/nitrogen gas stream (1–100 mL/min). The flow rates were selected such that the mixture composition was outside the explosive limits. The hot gaseous effluent from the reactor was cooled in a condenser tube cooled by circulating ethylene glycol/water at about −5° C. The condensed products were fed into a gas-liquid separator where the phases were separated. The gaseous stream containing unreacted oxygen, nitrogen and uncondensed acetone along with $CO_X$ products was vented through a reactor back pressure regulator and metered through a gas meter. The liquid product was pumped out of the gas-liquid separator and weighed. Both gas and liquid streams were analyzed by on-line gas chromatographs.

Conditions and Results

The 1% Pd/C catalyst was charged to the reactor (5 mL, 3.622 g, available from Engelhard, Inc., Type C3770). The feed to the reactor was acetone containing 1337 ppm acetaldehyde, 20 ppm propionaldehyde, 220 ppm methanol, and 206 ppm of other impurities, including cumene. The air feed rate was 12 mL/min. The temperature was 174° C. and the pressure was 47 psig (430 kPa). The impure acetone feed was introduced into the pre-heater/mixer tube as a liquid at a rate of 0.4 mL/min, resulting in a LHSV of 4.8 $h^{-1}$. Percent conversions of acetaldehyde, propionaldehyde, methanol and the percentage of oxidized acetone ("acetone burn") were calculated. The acetone burn was calculated using the assumption that all $CO_X$ products resulted from oxidation of acetone. The results are as follows:

| | |
|---|---|
| acetaldehyde | 100 |
| propionaldehyde | 100 |
| methanol | 79 |
| acetone burn | 0.1 |

Example 2

Abatement of Acetaldehyde, Propionaldehyde and Methanol in Acetone Using a 10% Pd/C Catalyst.

Four runs were performed in the reactor described in Example 1, but with pre-reduction of the catalyst at 250° C. in a 20 mL/min stream of 50% hydrogen/50% nitrogen for two hours. The 10% Pd/C catalyst was charged to the reactor (2 mL, 0.915 g, available from Aldrich Chem. Co., catalog #33010-8). In run 1 the feed to the reactor was acetone containing 1102 ppm acetaldehyde, 12 ppm propionaldehyde, and 263 ppm methanol; in runs 2–4, the acetone contained 1180 ppm acetaldehyde, 13 ppm propionaldehyde, and 280 ppm methanol. The reactor temperature was 150° C. in runs 1–3 and 200° C. in run 4; and the pressure was 0 psig (101 kPa) in all runs. The percent conversions of acetaldehyde ("A conv."), propionaldehyde ("P conv."), and methanol ("M conv.") in each run are as follows:

| Run No. | Acetone feed rate, mL/min. | Air feed rate, mL/min. | A conv. | P conv. | M conv. |
|---|---|---|---|---|---|
| 1 | 0.2 | 12 | 98.7 | 100 | 68.1 |
| 2 | 0.5 | 12 | 67.9 | 100 | 17.1 |
| 3 | 1 | 24 | 44.6 | 100 | 12.1 |
| 4 | 1 | 24 | 89.3 | 100 | 31.8 |

Example 3

Abatement of Acetaldehyde, Propionaldehyde and Methanol in Acetone Using a 1% Pt/C Catalyst.

Two runs were performed in the reactor described in Example 1, with pre-reduction of the catalyst as described in Example 2. The 1% Pt/C catalyst was charged to the reactor (4 mL, 2.075 g, available from Engelhard Co., Type C3653). In both runs the feed to the reactor was acetone containing 1362 ppm acetaldehyde, 13 ppm propionaldehyde, and 290 ppm methanol. The reactor temperature was 200° C. in run 1 and 250° C. in run 2; and the pressure was 0 psig (101 kPa) in both runs. The percent conversions of acetaldehyde ("A conv."), propionaldehyde ("P conv."), and methanol ("M conv.") in each run are as follows:

| Run No. | Acetone feed rate, mL/min. | Air feed rate, mL/min. | A conv. | P conv. | M conv. |
|---|---|---|---|---|---|
| 1 | 0.92 | 20 | 32.6 | 23.1 | 46.6 |
| 2 | 0.2 | 10 | 50.1 | 23.1 | 71.0 |

Example 4

Abatement of Acetaldehyde, Propionaldehyde and Methanol in Acetone Using a 1% Pd/C Catalyst.

Five runs were performed in the reactor described in Example 1, with pre-reduction of the catalyst as described in Example 2. The 1% Pd/C catalyst was charged to the reactor (4 mL, 2.832 g, available from Engelhard Co., Type C3770). In all runs the feed to the reactor was acetone containing 624 ppm acetaldehyde, 18 ppm propionaldehyde, and 466 ppm methanol; and the reactor temperature was 175° C. The pressure was 45 psig (412 kPa) in runs 1 and 4, 0 psig (101 kPa) in runs 2 and 5, and 20 psig (239 kPa) in run 3. The percent conversions of acetaldehyde ("A conv."), propionaldehyde ("P conv."), and methanol ("M conv.") in each run are as follows:

| Run No. | Acetone feed rate, mL/min. | Air feed rate, mL/min. | A conv. | P conv. | M conv. |
|---|---|---|---|---|---|
| 1 | 0.4 | 12 | 97.4 | 100 | 67.8 |
| 2 | 0.4 | 12 | 77.1 | 66.7 | 35.4 |
| 3 | 0.4 | 12 | 88.1 | 83.3 | 51.7 |
| 4 | 0.2 | 6 | 97.4 | 100 | 76.2 |
| 5 | 0.2 | 6 | 88.5 | 77.8 | 48.3 |

Example 5

Abatement of Acetaldehyde, Propionaldehyde and Methanol in Acetone a 1% Ru/C Catalyst.

One run was performed in the reactor described in Example 1, with pre-reduction of the catalyst as described in Example 2. The 1% Ru/C catalyst was charged to the reactor (10 mL, 498 g, available from Engelhard Co., Type C4023). The feed to the reactor was containing 1323 ppm acetaldehyde, 18 ppm propionaldehyde, and 235 ppm methanol; the reactor temperature was 175° C; and the pressure was 45 psig (412 kPa). The acetone feed rate was 0.2 mL/min. and the air feed rate was 6 mL/min. Percent conversions were as follows:

| | |
|---|---|
| acetaldehyde | 3.9 |
| propionaldehyde | 16.7 |
| methanol | 42.1 |

Example 6

Abatement of Acetaldehyde, Propionaldehyde and Methanol in Acetone Using Manganese Granules as a Catalyst.

Two runs were performed in the reactor described in Example 1, with pre-reduction of the catalyst as described in Example 2. The manganese catalyst was charged to the reactor (99.99%, 10 mL, 41.063 g, available from Alfa Inc., catalog #36125). In all runs the feed to the reactor was acetone containing 1495 ppm acetaldehyde, 21 ppm propionaldehyde, and 242 ppm methanol; and the pressure was 45 psig (412 kPa). The reactor temperature was 250° C. in run 1 and 350° C. in run 2. The percent conversions of acetaldehyde ("A conv."), propionaldehyde ("P conv."), and methanol ("M conv.") in each run are as follows:

| Run No. | Acetone feed rate, mL/min. | Air feed rate, mL/min. | A conv. | P conv. | M conv. |
|---|---|---|---|---|---|
| 1 | 0.4 | 12 | 3.4 | 4.8 | 5.0 |
| 2 | 0.2 | 12 | 42.1 | 38.1 | N/A* |

*The methanol level increased to 8.5 times the original level in this run, indicating that the catalyst induces generation of additional methanol at higher temperatures.

Example 7

Abatement of Acetaldehyde, Propionaldehyde and Methanol in Acetone Using a 2% Pd/silica Catalyst.

One run was performed in the reactor described in Example 1, with pre-reduction of the catalyst as described in Example 2. The 2% Pd/silica catalyst was charged to the reactor (5 mL, 1.985 g, available from Engelhard Co., Type C5032). The feed to the reactor was acetone containing 1283 ppm acetaldehyde, 18 ppm propionaldehyde, and 214 ppm methanol; the reactor temperature was 173° C; and the pressure was 45 psig (412 kPa). The acetone feed rate was 0.4 mL/min. and the air feed rate was 12 mL/min. Percent conversions and the percentage of oxidized acetone ("acetone burn") were as follows:

| | |
|---|---|
| acetaldehyde | 91.2 |
| propionaldehyde | 100 |
| methanol | 75.7 |
| acetone burn | 0.2 |

Example 8

Abatement of Acetaldehyde, Propionaldehyde and Methanol in Acetone Using a 0.5% Pd/alumina Catalyst.

One run was performed in the reactor described in Example 1. The 0.5% Pd/alumina catalyst was charged to the reactor (2 mL, 2.185 g, available from Engelhard Co., Type S/O 29119, α-alumina). The feed to the reactor was acetone containing 1340 ppm acetaldehyde, 19 ppm propionaldehyde, and 237 ppm methanol; the reactor temperature was 179° C.; and the pressure was 48 psig (432 kPa). The acetone feed rate was 0.4 mL/min. and the air feed rate was 12 mL/min. Unidentified impurities were detected in the product at a level of 122 ppm, assuming the impurities had the same response factor as acetaldehyde. Percent conversions and the percentage of oxidized acetone ("acetone burn") were as follows:

|             |       |
|-------------|-------|
| acetaldehyde | 96.4 |
| propionaldehyde | 100 |
| methanol | 59.5 |
| acetone burn | 0.1 |

Example 9

Abatement of Acetaldehyde, Propionaldehyde and Methanol in Acetone Using a 0.5% Pd/alumina Catalyst.

One run was performed in the reactor described in Example 1. The 0.5% Pd/alumina catalyst was charged to the reactor (2.6 mL, 2.196 g, available from Engelhard Co., Type C3677, γ-alumina). The feed to the reactor was acetone containing 1383 ppm acetaldehyde, 0 ppm propionaldehyde, 265 ppm methanol and 150 ppm of other impurities; the reactor temperature was 175° C; and the pressure was 45 psig (412 kPa). The acetone feed rate was 0.4 mL/min. and the air feed rate was 12 mL/min. Percent conversions and the levels of other impurities in ppm are given below after 1.5 hours and after 16.5 hours. The percentage of oxidized acetone ("acetone burn") after 16.5 hours is also provided below.

|                  | 1.5 hrs. | 16.5 hrs. |
|------------------|----------|-----------|
| acetaldehyde     | 99.8     | 100       |
| propionaldehyde  | N/A      | N/A       |
| methanol         | 77.7     | 71.7      |
| acetic acid      | 17 ppm   | 1096 ppm  |
| other impurities | 4330 ppm | 222 ppm   |
| acetone burn     |          | 0.1       |

The preceding Examples are intended to describe certain preferred embodiments of the present invention. It should be appreciated, however, that obvious additions and modifications of the invention will be apparent to one skilled in the art. The invention is not limited except as set forth in the claims.

What is claimed is:

1. A method for purification of acetone containing at least one oxidizable impurity; said method comprising steps of:

(a) contacting acetone containing at least one oxidizable impurity with a heterogeneous oxidation catalyst in the presence of oxygen for a time and at a temperature sufficient to oxidize at least a portion of at least one oxidizable impurity; and (b) substantially separating purified acetone from a mixture obtained from step (a).

2. The method of claim 1 in which purified acetone is separated from the mixture by distillation.

3. The method of claim 2 in which said at least one oxidizable impurity comprises acetaldehyde, propionaldehyde and methanol.

4. The method of claim 3 in which said heterogeneous oxidation catalyst comprises at least one metal on a support selected from the group consisting of carbon and inorganic supports.

5. The method of claim 4 in which said heterogeneous oxidation catalyst comprises at least one metal on a support selected from the group consisting of alumina and silica supports.

6. The method of claim 5 in which said acetone containing at least one oxidizable impurity contains less than about 1000 ppm of aldehyde impurities and less than about 500 ppm methanol.

7. The method of claim 6 in which said at least one metal comprises a precious metal.

8. The method of claim 7 in which substantially all of the acetone containing oxidizable impurities is in the vapor phase.

9. The method of claim 8 in which said precious metal comprises palladium.

10. The method of claim 9 in which said support comprises α-alumina.

11. A method according to claim 1, wherein the acetone containing at least one oxidizable impurity is contacted with a heterogeneous oxidation catalyst in the presence of oxygen at a temperature above about 50° C., and below about 250° C.

* * * * *